United States Patent
Lee

(10) Patent No.: US 9,149,634 B2
(45) Date of Patent: Oct. 6, 2015

(54) DEVICE FOR STRENGTHENING PELVIC FLOOR MUSCLES AND METHOD FOR CONTROLLING THE SAME

(71) Applicant: Alpha Medic Co., Ltd., Daegu (KR)

(72) Inventor: Chang-Doo Lee, Daegu (KR)

(73) Assignee: ALPHA MEDIC CO., LTD., Daegu (KR)

( * ) Notice: Subject to any disclaimer, the term of this patent is extended or adjusted under 35 U.S.C. 154(b) by 0 days.

(21) Appl. No.: 13/829,166

(22) Filed: Mar. 14, 2013

(65) Prior Publication Data

US 2014/0155954 A1 Jun. 5, 2014

(30) Foreign Application Priority Data

Dec. 3, 2012 (KR) ......................... 10-2012-0139026

(51) Int. Cl.
*A61N 1/04* (2006.01)
*A61N 1/36* (2006.01)
*A47K 13/24* (2006.01)

(52) U.S. Cl.
CPC ............ *A61N 1/36014* (2013.01); *A47K 13/24* (2013.01); *A61N 1/0452* (2013.01); *A61N 1/36007* (2013.01)

(58) Field of Classification Search
CPC . A61N 1/0524; A61N 1/0512; A61N 1/0514; A61N 1/0521; A61N 1/36007; A61N 1/36107; A61N 1/0452
USPC ...................................................... 607/48, 138
See application file for complete search history.

(56) References Cited

U.S. PATENT DOCUMENTS

| | | | |
|---|---|---|---|
| 4,983,814 A * | 1/1991 | Ohgushi et al. | 219/545 |
| 6,553,266 B1 * | 4/2003 | Yuang | 607/138 |
| 8,494,658 B2 * | 7/2013 | Crowe et al. | 607/138 |

\* cited by examiner

*Primary Examiner* — Paula J Stice
(74) *Attorney, Agent, or Firm* — Patent Office of Dr. Chung Park

(57) ABSTRACT

Provided is a device for strengthening a pelvic floor muscle. The device for strengthening a pelvic floor muscle includes a device body provided with a seating means on which a user can sit; and two or more electrode pads for applying a low frequency pulse, the electrode pads being disposed around a portion of the device body corresponding to the user's anus. In addition, a method for controlling the device for strengthening a pelvic floor muscle includes separately applying the generated low frequency pulse in a ramp up (Ru) time, a hold (Ht) time and a ramp down (Rd) time.

14 Claims, 14 Drawing Sheets

RELATION BETWEEN A TIME AND A CONTRACTILE
FORCE ACCORDING TO A FREQUENCY

RELATION BETWEEN A PULSE WIDTH AND A MUSCLE CONTRACTION
ACCORDING TO A VARIATION OF STIMULATION INTENSITY

CIRCUIT BLOCK DIAGRAM 1

PULSE SIGNAL WAVEFORM DIAGRAM

CIRCUIT BLOCK DIAGRAM 2

CIRCUIT BLOCK DIAGRAM 3

DEVICE FOR STRENGTHENING PELVIC FLOOR MUSCLES AND METHOD FOR CONTROLLING THE SAME

CROSS-REFERENCE TO RELATED APPLICATION

This application claims priority to and the benefit of Korean Patent Application No. 2012-0139026, filed on Dec. 3, 2012, the disclosure of which is incorporated herein by reference in its entirety.

BACKGROUND

1. Field of the Invention

The present invention relates to a device for strengthening pelvic floor muscles, and more particularly, a device for strengthening pelvic floor muscles which can strengthen pelvic floor muscles through electrical stimulation of an ordinary low frequency pulse to provide various improvement effects of a human body, for example, a health promotion function such as smooth defecation, an improvement of sexual function, prevention and treatment of urinary incontinence and a massage of a prostate area.

2. Discussion of Related Art

Various types of therapy devices for repeatedly applying electrical stimulation generated using a low frequency pulse to a human body to promote various effects have been conceived of and utilized.

In such conventional therapy devices, a user sits on a holder having a low frequency pulse generating unit and a therapy site is in contact with the holder. The therapy device having the above structure and utilizing an electrical signal processing has been conceived of and filed as a patent application.

Muscles corresponding to the bottom of the pelvis are known as pelvic floor muscles, and therapy devices utilizing a low frequency pulse have been conceived of as known methods for strengthening the pelvic floor muscles. In addition, various kinds of devices have been developed and utilized according to the therapy sites of human body and the intended use.

However, studies and research on a mechanical structure suitable for a device which can easily strengthen the pelvic floor muscles through general home use and for an effective low frequency pulse have not been performed, and only an effect caused by applying the low frequency can be expected.

Some of the devices according to the conventional technology have a structure to be inserted into a vagina of woman. However, this kind of device is disadvantageous in that it is difficult to use this kind of device, a man cannot utilize this device and this device has a vulnerable mechanism.

SUMMARY OF THE INVENTION

The present invention is conceived to solve the problems of the above conventional technology, and an object of the present invention is to provide a device for fundamentally strengthening pelvic floor muscles through electrical stimulation with an ordinary low frequency pulse and a method for controlling the same, whereby the pelvic floor muscles are electrically stimulated and the pelvic floor muscles of the human body are strengthened through a stimulation cycle in which contraction and a relaxation and rest time are repeated to obtain various additional effects.

As the above effects, due to a strengthening of the pelvic floor muscles, smooth defecation, prevention and treatment of urinary incontinence and improvement of sexual function are promoted, a massage function for the prostate is obtained, and the user can conveniently utilize the device in a state in which the user sits on the device or defecates into the toilet bowl.

In addition, by providing the mode in which the user can variously select the intensity, time and level of the low frequency pulse to be applied, the user can passively obtain a therapeutic effect while the user conducts other affairs.

In addition, an electrode pad is in close contact with not only a user's levator ani but also the user's coccyx so that the low frequency pulse can be effectively applied to the levator ani and the coccygeal muscle to effectively strengthen all of the pelvic floor muscles.

In order to achieve the above objects, a device for strengthening the pelvic floor muscles according to the present invention includes a device body provided with a seating means on which a user can sit; and two or more electrode pads for applying the low frequency pulse, the electrode pads being disposed around a portion of the device body corresponding to the user's anus.

In order to achieve the above objects, in addition, a method for controlling a device for strengthening the pelvic floor muscles according to the present invention includes separately applying the generated low frequency pulse in a ramp up (Ru) time, a hold (Ht) time and a ramp down (Rd) time.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Figure 1:
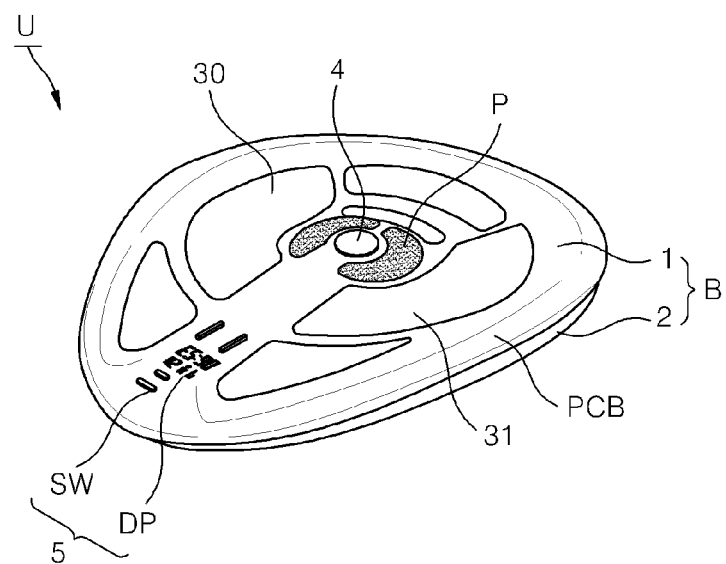
FIG. 1 is a perspective view showing an appearance of one embodiment of a device for strengthening the pelvic floor muscles according to the present invention.
Figure 2:
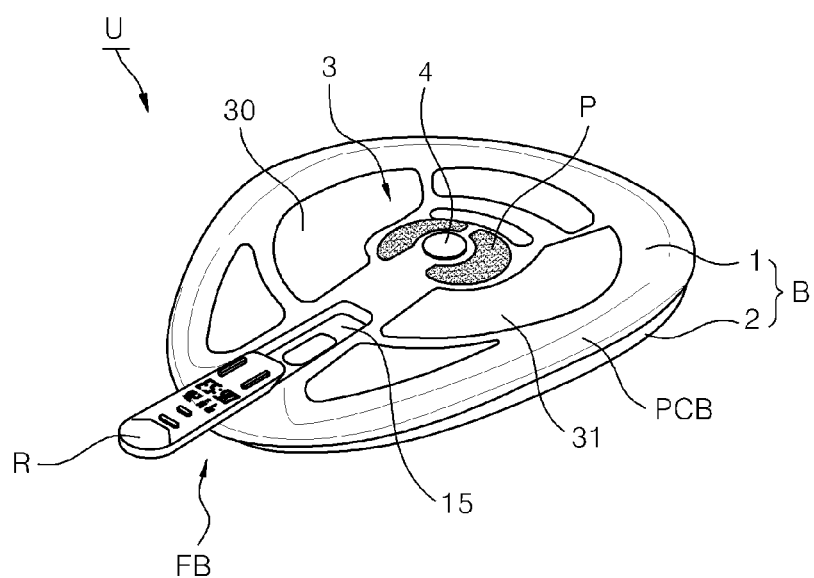
FIG. 2 is a perspective view showing an appearance of another embodiment of a device for strengthening the pelvic floor muscles employing a remote controller according to the present invention.
Figure 3:
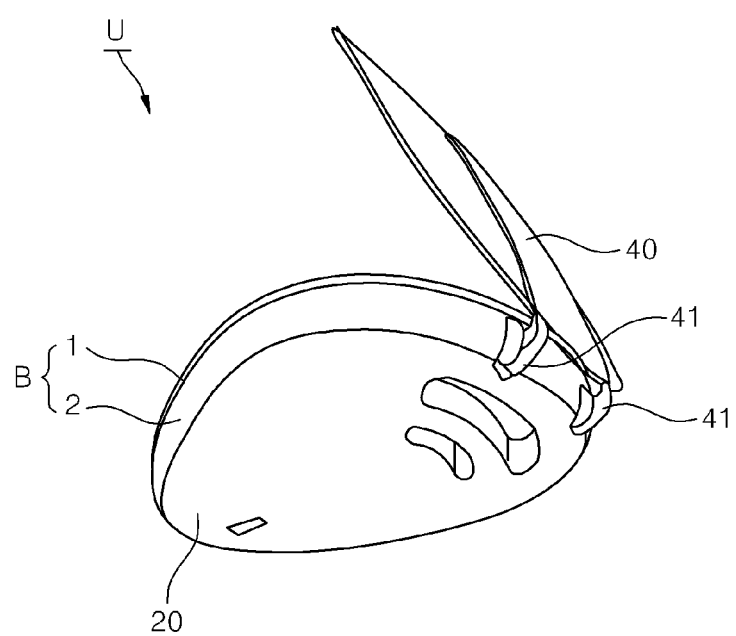
FIG. 3 is a bottom perspective view showing an appearance of one embodiment of a device for strengthening the pelvic floor muscles according to the present invention.
Figure 4:
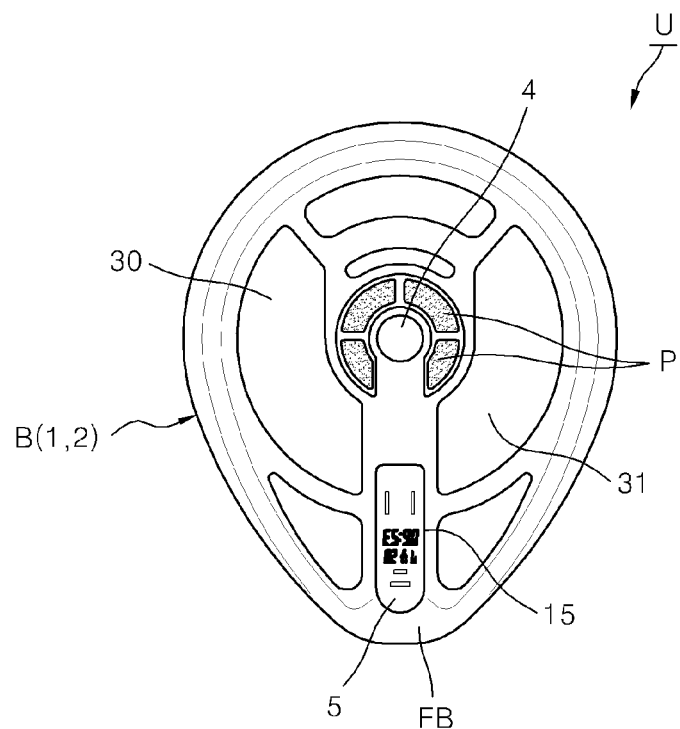
FIG. 4 is a plan view of an embodiment of a device for strengthening the pelvic floor muscles according to the present invention.
Figure 5:
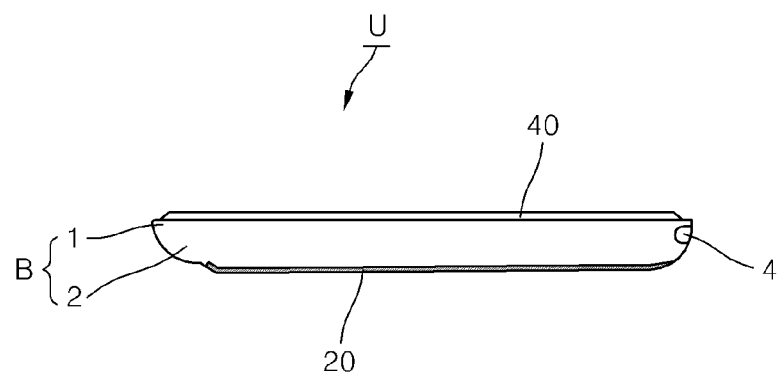
FIG. 5 is a side view of FIG. 4.
Figure 6:
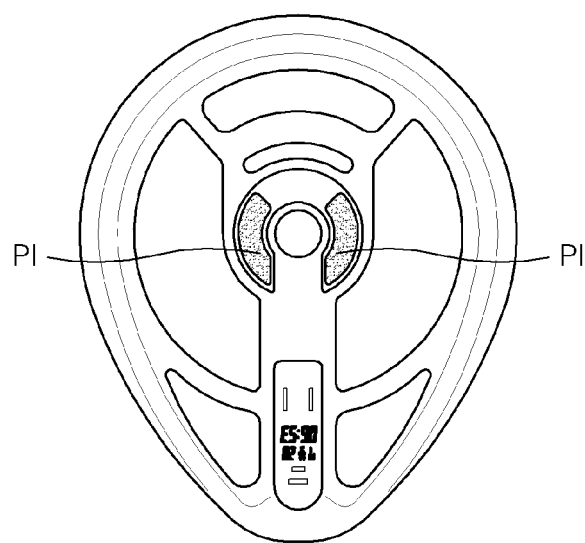
FIG. 6 is a plan view and a structural view of a first embodiment of an arrangement of electrodes of a device for strengthening the pelvic floor muscles according to the present invention.
Figure 6:
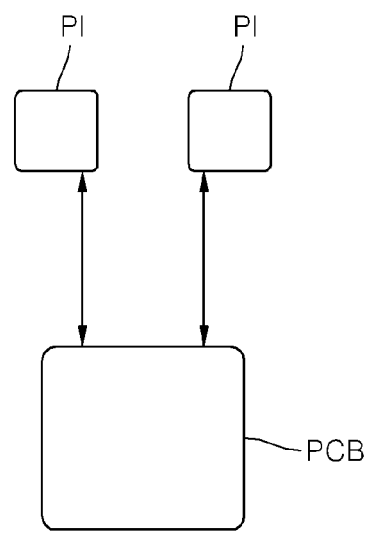
Figure 7:
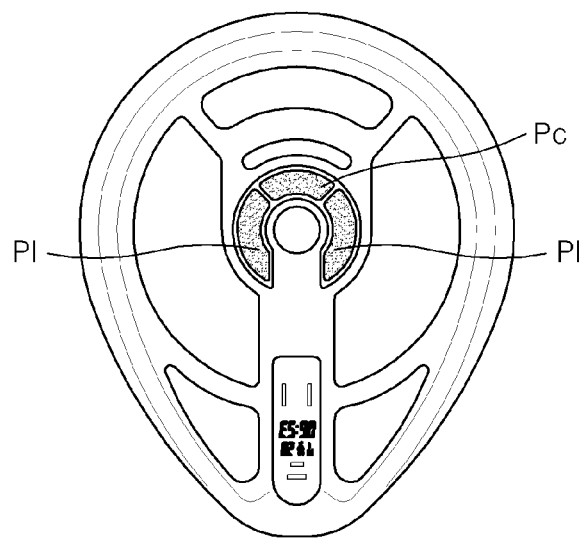
FIG. 7 is a plan view and a structural view of a second embodiment of an arrangement of electrodes of a device for strengthening the pelvic floor muscles according to the present invention.
Figure 7:
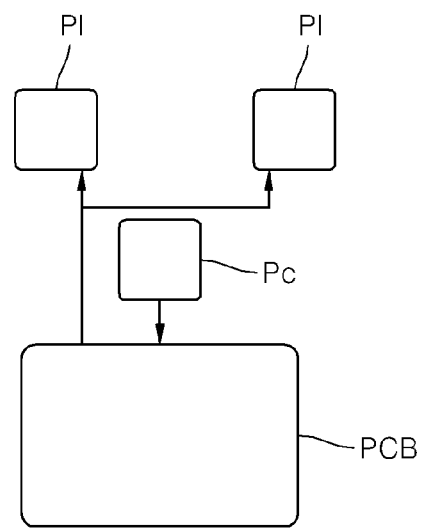
Figure 8:
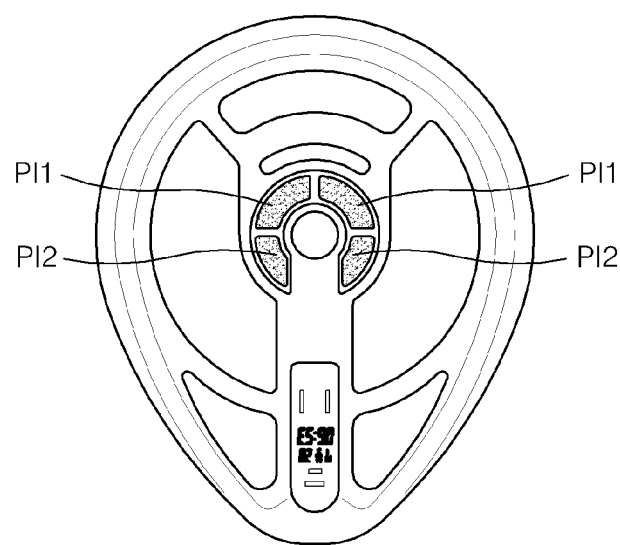
FIG. 8 is a plan view and a structural view of a third embodiment of an arrangement of electrodes of a device for strengthening the pelvic floor muscles according to the present invention.
Figure 8:
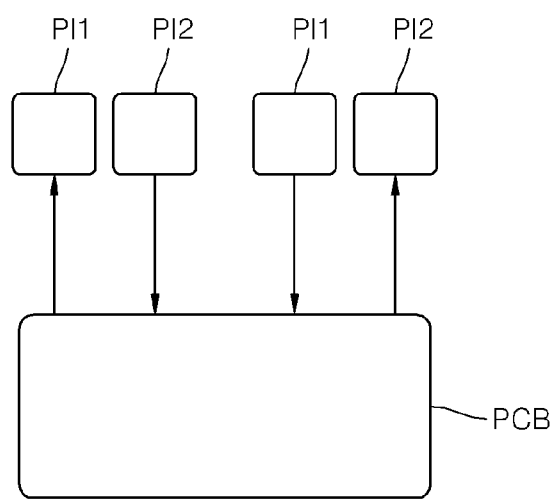
Figure 9:
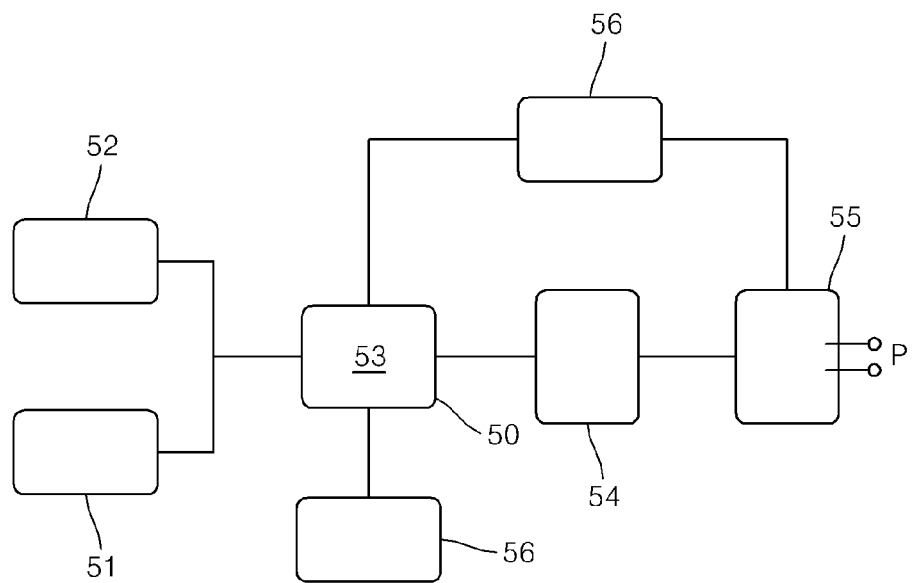
FIG. 9 is a block diagram for illustrating a structure of a circuit part of a device for strengthening the pelvic floor muscles according to the present invention.
Figure 10:
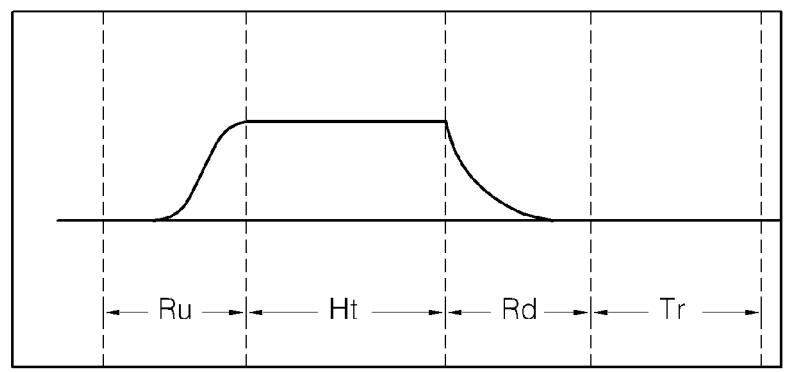
FIG. 10 is a graph showing a low frequency pulse generated in a circuit part of a device for strengthening the pelvic floor muscles according to the present invention.
Figure 11:
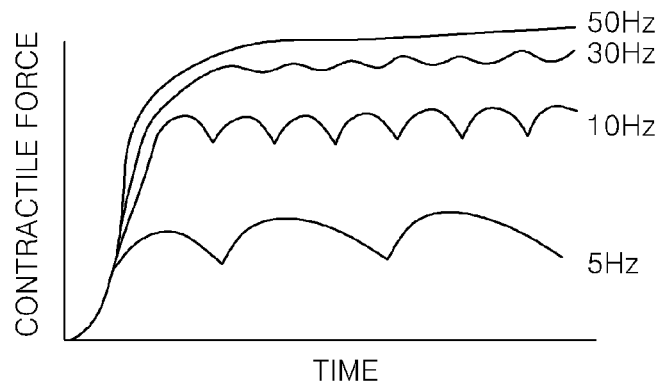
FIG. 11 is a graph showing a result of clinical research on a device for strengthening the pelvic floor muscles according to the present invention and a relation between a time and a contractile force according to a frequency.
Figure 12:
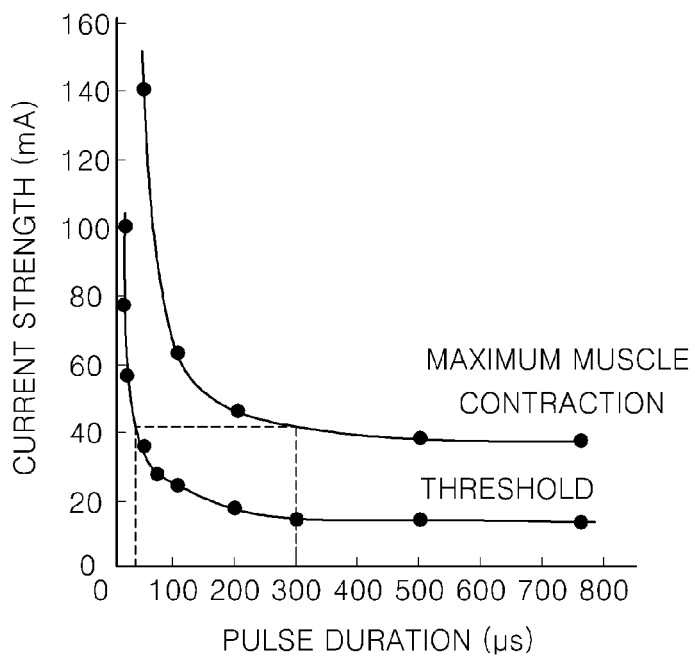
FIG. 12 is a graph showing a result of clinical research on a device for strengthening the pelvic floor muscles according to the present invention and a relation between a pulse width and a muscle contraction according to a variation of stimulation intensity.
Figure 13:
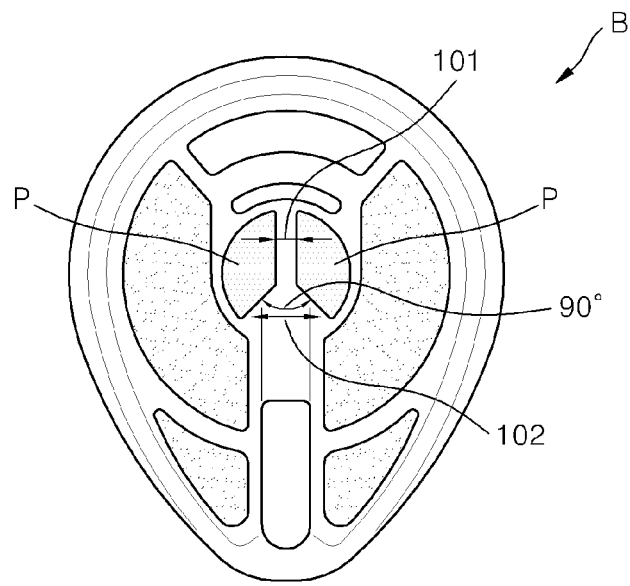
FIG. 13 is a plan view of a device for strengthening the pelvic floor muscles according to another embodiment of the present invention.

FIG. 1 is a perspective view showing an appearance of one embodiment of a device for strengthening the pelvic floor muscles according to the present invention, FIG. 2 is a perspective view showing an appearance of another embodiment of a device for strengthening the pelvic floor muscles employing a remote controller according to the present invention, FIG. 3 is a bottom perspective view showing an appearance of one embodiment of a device for strengthening the pelvic floor muscles according to the present invention, FIG. 4 is a plan view of an embodiment of a device for strengthening the pelvic floor muscles according to the present invention, FIG. 5 is a side view of FIG. 4, FIG. 6 is a plan view and a structural view of a first embodiment of an arrangement of electrodes of a device for strengthening the pelvic floor muscles according to the present invention, FIG. 7 is a plan view and a structural view of a second embodiment of an arrangement of electrodes of a device for strengthening the pelvic floor muscles according to the present invention, FIG. 8 is a plan view and a structural view of a third embodiment of an arrangement of electrodes of a device for strengthening the pelvic floor muscles according to the present invention, FIG. 9 is a block diagram for illustrating a structure of a circuit part of a device for strengthening the pelvic floor muscles according to the present invention. FIG. 10 is a graph showing a low frequency pulse generated in a circuit part of a device for strengthening the pelvic floor muscles according to the present invention, FIG. 11 is a graph showing a result of clinical research on a device for strengthening the pelvic floor muscles according to the present invention and a relation between a time and a contractile force according to a frequency, FIG. 12 is a graph showing a result of clinical research on a device for strengthening the pelvic floor muscles according to the present invention and a relation between a pulse width and a muscle contraction according to a variation of stimulation intensity, and FIG. 13 is a plan view of a device for strengthening the pelvic floor muscles according to another embodiment of the present invention.

Prior to explaining a specific structure of the present invention, a structure and characteristics of a portion adjacent to a basic pelvis of a human body for embodying a technical idea of the present invention will be briefly illustrated.

Organs in the pelvis of human body are supported by muscles around the perineum and muscles of the pelvic diaphragm. The pelvic diaphragm consists of the pubococcygeus muscle, the iliococcygeal muscle, the ischiococcygeus muscle and the coccygeus muscle, which make up the levator ani muscle, to form a sling of muscles in the form of retiform bed and support the organs in the pelvis. The pelvic ligaments are not true ligaments, but are actually compressed endopelvic fasciae covering the pelvic structure and may be regarded as a neurovascular bundle having a holding function.

The pelvic floor muscles provide the pelvic structure with a supporting force together with the pelvic ligaments, and pelvic floor muscle exercises utilized for conventional urinary incontinence therapy strengthen the pelvic floor muscles and improve sexual functions As such pelvic floor muscle exercises, exercises known as "Kegel exercises" are highly effective and play an important role in a therapy and prevention of urinary incontinence. Many studies on the above exercises have been and continue to be published. The pelvic floor muscles support organs including the urethra, the urinary bladder and the uterus, and relate to sexual functions.

If the pelvic floor muscles are damaged, not only stress incontinence but also sexual dysfunction may occur. Scientific research has also been published showing that pelvic floor muscle exercises are beneficial for men with erectile dysfunction. In 1993, a medical team in England compared an effect of vein surgery with an effect of pelvic floor muscle exercises for 150 patients diagnosed with venous sexual dysfunction It is assumed that the pelvic floor muscle exercises affect sexual function because the penis is pressurized to prevent blood from escaping from the penis. Among the pelvic floor muscles, the ischiocavernosus muscle and the bulbospongiosus muscle are involved in erection of the penis.

The ischiocavernosus muscle connects the pelvic bones to the penis, and the bulbospongiosus muscle wraps around the penis. These muscles are simultaneously contracted when the anus is strained. Considering a relation between the pelvic floor muscles and sexual dysfunction in women, Dr. Master and Dr. John defined that a woman's orgasm is a response manifested in the vagina by a contraction of the pelvic floor muscles, and Dr. Boucier asserted that there is a meaningful correlation between a tensile force of the pelvic floor muscles and sexual gratification.

In order to stimulate the pelvic floor muscles, a relatively sophisticated method is required. The basic technical spirit of exercises for strengthening the pelvic floor muscles provided by the present invention is to strengthen the pelvic floor muscles by increasing a volume of the pelvic floor muscles.

The present invention is conceived for strengthening the pelvic floor muscles, which has been difficult to provide in the conventional technology as described above, and an object of the present invention is to provide an exercise program suitable for strengthening the pelvic floor muscles through one electrode pad with one polarity and another electrode pad with the other polarity disposed at a right side and a left side of the perineum (two polarities), two electrode pads with one polarity and two electrode pads with the other polarity alternatively disposed at a lower portion and an upper portion of a left side and a lower portion and an upper portion of a right side of the perineum (four polarities), or two electrode pads with different polarities and one common electrode pad disposed between two electrode pad (three polarities).

The device for alleviating pain utilizing the low frequency pulse stimulates the sensory nerves to block a pain signal transmitted through the sensory nerves. Accordingly, the above device utilizes a current having a regular and accurate cycle of several times to several hundred times a second.

At this time, the low frequency pulse current is transmitted to the sensory nerves as well as the motor nerves around the sensory nerves so that the surrounding muscles are moved. The above motion of the muscle is only an electrical response to the stimulation and differs from the movement caused by the exercise, and the muscle is never strengthened by this responsive motion of the muscle.

The motor nerve is located deep within the human body, and thus, in order to control the motor nerve, the contact conductive pads should be attached to skin of the human body to allow the pads to correspond to beginning and end points of the motor nerve. The placement of the conductive pad should be based on a location of the relevant muscle to be strengthened and an origin segment and insertion segment of the relevant muscle rather than a shape or a deviation of the contact portion of the conductive pad. In addition, the low frequency pulse current stimulation depends on various pulse parameters including a pulse duration, a pulse frequency, a ramp time and a cyclic period. Thus, in order to stimulate the motor nerve located deep within the human body, the most suitable parameters should be selected.

Results of research on a physiologic contraction of the muscle fiber indicated that type II fiber is moved by a contraction for 10 seconds or more, but type I fiber is more effectively moved by a contraction for 3 to 6 seconds, and thus it is helpful to utilize both short contraction movement and long contraction movement (Dougherty, 1998).

According to clinical research, although the frequency causing a tetanic contraction varies slightly according to the muscles as shown in FIG. 11 and FIG. 12, the tetanic contraction is most effectively caused at a frequency of 30 to 80 Hz. In addition, according to clinical research, if the pulse width is larger than 500 μs, a subject feels discomfort, and the frequency with a pulse of 100 to 500 μs is most efficient at comfortably causing the muscle contraction with minimal current strength.

A concrete structure of a device U for strengthening the pelvic floor muscles conceived on the basis of the basic spirit of the present invention as above is illustrated in detail with reference to FIG. 1.

Like a conventional case body, as shown in FIG. 1, a device body B is an injection-molded body made of fibrous tissue or synthetic resin and consists of an upper body case 1 and a lower body case 2. This device body has a structure having an inner hollow part for receiving a circuit board (PCB) on which an electrical circuit provided for operating the device is arranged. The electrical circuit will be described below.

This device body B is constructed such that various planar shapes may be employed as a design of the entire device body. As shown in the drawing, however, an oval-shaped body with a front body part FB having a slightly sharp front side is constructed as the device body to enhance user accessibility and to minimize a corner portion, thereby minimizing damage to the user's body. In addition, it goes without saying that the device body B may be formed of a fabric material such as a cushion.

Furthermore, the device body B comes in contact with an anal region of the user. Thus, the device body may be cleaned to prevent contamination and infection and may be waterproofed to prevent water from being entering when the device body is cleaned with water.

It is preferable that the upper body case 1 has a seating recess part 3 which is curved toward an inside like a saddle and is suitable for seating and treating the user, to give the user comfort when the user sits on the upper body case.

As a contact preventing means, a contact preventing through hole 4 is provided at and passes vertically through a central portion of the upper body case 1 to allow an electrode to communicate with the lower body case 2 so that contact between the unsanitary region of the anus and the upper body case is minimized when a plurality of persons (typically family members) utilize this device. Instead of the through hole, of course, a simple recess can be used as this contact preventing means to prevent the user's skin from coming in contact with the upper body case.

On the other hand, an electrode pad P according to an object of the present invention is formed of conductive material, and a hydrogel type electrode, a silicon+carbon coating type electrode or a metal electrode is provided on a main body. For example, a gel pad, carbon (carbon rubber) or metal may be employed as material for the electrode pad D, and the electrode pad may be formed of a wet sponge.

It is preferable to provide an elastic lower part 20 coated or covered with an elastic material such as rubber, silicon, urethane and the like on a lower surface of the lower body case 2 constituting a lower part of the device body B to prevent the device body from being damaged and to absorb a shock when the device body is placed on a hard floor, a hard toilet seat and a hard toilet cover.

An operation panel part 5 having a plurality of selection switches SW and a display DP is provided on the front body part FB, and the user can manipulate the plurality of selection switches to operate a circuit part (described below) for selecting a level of a strengthening training program, an intensity of the lower frequency pulse to be applied, an operating time and the like.

As another optional structure, as shown in FIG. 2, a slit 15 with a length for receiving a remote controller C is formed on the front body part FB so that the remote controller C is received in the slit when the user does not use the device, or the user can manipulate the remote controller which is received in the slit when utilizing the device. In addition, an additional remote controller can be provided.

As another embodiment, as shown in a bottom perspective view of FIG. 3, a body cover 40 is provided on an upper end portion of the device body B, and this body cover is hingedly rotated by a hinge lever 41. Providing this body cover 40 makes it possible to prevent foreign substance from attaching to the upper body case 1 or to improve an appearance of the device when the device is not utilized.

In the device U for strengthening the pelvic floor muscles of the present invention having the above mechanical structure, a structure and control of the electrode pad P for applying the electrical stimulation to the user' pelvic floor muscles are illustrated.

The circuit part which controls the electrode pad P for generating the electrical stimulation may be variously configured. As one example, as shown in FIG. 9, the circuit part includes a control unit 50 performing a main controlling process, a key input unit 51 which is the operation panel part 5 through which the user inputs the data on the level of the strengthening training program, the intensity of lower frequency pulse and the operating time to the control unit 50, a display unit 52 such as an LED display for displaying the input values and the current set status, the control unit 50 such as a central processing unit (CPU) in which a control program 53 for storing a generation status of the low frequency pulse selected variously by the user and controlling the low frequency pulse is stored, an electrical signal generating unit 54 for generating the low frequency pulse acting as the electrical stimulation, and an output signal detecting/comparing unit 56 having the printed circuit board (PCB) on which a commercial frequency output unit 55, which is the electrode pad P, is provided. Here, the output signal detecting/comparing unit 56 compares an intensity of the low frequency pulse which is pre-set in the control unit 50 with an intensity of the low frequency pulse which is actually generated in the electrical signal generating unit 54 and applied to the user, and performs a feedback process until the intensity of the actual low frequency pulse reaches the preset intensity.

An arrangement of polarities of the electrode pads P and a method for controlling the low frequency pulse can be variously achieved. The arrangement of polarities of the electrode pads may be selected from a structure having two electrode pads Pl and Pr as shown in FIG. 6, a structure having three electrode pads Pl, Pc and Pr as shown in FIG. 7 and a structure having four electrode pads Pl1, Pl2, Pr1 and Pr2 as shown in FIG. 8.

In the structure having two electrode pads Pl and Pr as shown in FIG. 6, at least two electrode pads adjacent to the ischia and the pubic arch of the human body are arranged side by side at a certain interval. Between the right and left ischia, in this structure, two electrode pads Pl and Pr can transmit and receive the low frequency pulse passing through a resistance of the human body to stimulate the pelvic floor muscles so that the pelvic floor muscles can be strengthened by continuous training.

When two electrode pads Pl and Pr are used, the exemplary control program 53 stored in the control unit 50 may be as below.

In order to ideally realize an object of the device U for strengthening the pelvic floor muscles of the present invention, as shown in FIG. 10, a low frequency pulse operating time consists of a ramp up time Ru, a hold time Ht, a ramp down time Rd and a rest time Tr. It is preferable to generate the electrical signal with a frequency of 0 to 100 Hz and a pulse width of 100 µs to 500 µs. In order to stimulate the motor nerve located more deeply within the body, the low frequency signal and the mid frequency signal of 1,000 to 2,000 Hz superimposed on each other may be utilized.

By an operation of the output signal detecting/comparing unit 56 which compares an intensity of the low frequency pulse pre-set in the control unit 50 of the circuit part with an intensity of the low frequency pulse which is actually generated in the electrical signal generating unit 54 and applied to the user, and performs a feedback process until the intensity of the actual low frequency pulse reaches the preset intensity, the actually generated low frequency pulse forms a saw tooth waveform through a minute feedback supplement, and this saw tooth waveform provides the user with the time required for adapting to the low frequency pulse and becomes a preferable waveform.

The ramp up time corresponds to a warming-up (an exercise for relaxing the body) which is necessarily performed when a person exercises safely, and the ramp down time is a cool-down process performed after completing an exercise. By providing the above processes, the user is not surprised by the current and does not feel unpleasant.

If the user uses the low frequency pulse without such a program, there is concern of side effects caused by excessive use or misuse of the low frequency pulse and it is difficult to obtain a satisfactory effect so that the present invention employs the above basic control.

As shown in the table below, the preferable set of the time is that every time a level of the training program selected by the user is elevated, the operating time is increased. At this time, since it is important to adjust the hold time during the operating time, the hold time is adjusted, the rest time is increased in proportion to the operating time and the total contraction time is increased to easily achieve the desired purpose

TABLE 1

| Program | One cycle (Unit: Second) | | | | Operating time |
|---|---|---|---|---|---|
| | Hold time | | Rest time | | 5 min |
| 1 | 1 | 1 | 1 | 3 | 10 min. |
| 2 | 1 | 2 | 1 | 4 | 15 min. |
| 3 | 1 | 3 | 1 | 5 | 15 min. |
| 4 | 1 | 4 | 1 | 6 | 15 min. |
| 5 | 1 | 5 | 1 | 7 | 15 min. |
| 6 | 1 | 10 | 1 | 12 | 15 min. |
| 7 | 1 | 15 | 1 | 17 | 15 min. |

In order to effectively strengthen the bilaterally symmetrical pelvic floor muscles, in view of characteristics of the human body, the device U for strengthening the pelvic floor muscles of the present invention may employ a two-sided-arrangement method in which the conductive electrode pads are disposed on the right ischium and the left ischium of the hip bone placed at both sides of the perineum (the method in which a pair of electrode pads are symmetrically disposed on right and left portions of the body), or a three-polarity-arrangement method in which a negative electrode pad is commonly disposed on the coccyx portion between the right and left electrode pads, or a method in which four (4) or more electrode pads are alternatively disposed on upper and lower portions of each of both side portions.

As described above, a portion which is fixed when the muscle is contracted is called an "origin point" and a portion which moves when the muscle is contracted is called an "insertion point." Like the above, since skeletal muscles are attached to bones, the operator must know the origin point and the insertion point to easily understand an operation of the muscles and the nerves controlling this muscles.

In terms of the pelvic floor muscles on right and left sides of the levator ani muscle, by the two-polarity arrangement in which two electrode pads P are disposed at right and left sides (two polarities) or the electrode pads are disposed at upper and lower portions of the right side and at upper and lower portions of the left side (four polarities) or by the three-polarity arrangement in which two electrode pads are disposed at right and left sides and one electrode pad is commonly utilized, the operator can frequently change the polarities of the electrode pads without any medical understanding to effectively strengthen the right and left pelvic floor muscles. Such electrode pads P may be variously preset by a control of the control program of the printed circuit board PCB.

On the basis of the above fundamental technical spirit, an arrangement of the electrode pads according to the present invention is illustrated. In the structure consisting of three (3) electrode pads Pl, Pc and Pr as shown in FIG. 8, the above setting means is provided and the electrode pad Pc, which is the central electrode, is placed at a part of the coccyx or a portion adjacent to the coccyx.

At this time, the low frequency pulse is applied to the pair of electrode pads Pl and Pc or the pair of electrode pads Pr and Pc, and only one pulse signal is generated in the circuit part of the printed circuit board PCB. This generated pulse signal is commonly applied to the electrode pad Pl—the electrode pad Pc and the electrode pad Pr—the electrode pad Pc and then returned through the electrode pad Pc, which is a central electrode and acts as a common return point.

In the embodiment of the electrode pad P, ratios of the pulse signals flowing through the electrode pads Pl and Pr which are the side electrodes may or may not be similar to each other according to an impedance between the electrode pads (Pl–Pr) which are the side electrodes and the electrode pad Pc which is the central electrode and an impedance between each side electrode and the skin of the human body.

As shown in FIG. 8, the electrode pad P of another embodiment may consist of four (4) electrode pads Pl1, Pl2, Pr1, and Pr2 in pairs of the electrode pads Pl1 and Pl2 and the electrode pads Pr1 and Pr2.

The first pulse signal is applied to the pair of electrode pads Pl1 and Pl2 and the second pulse signal is applied to the other pair of electrode pads Pr1 and Pr2. A magnitude and width of the first pulse signal may differ from or may be the same as those of the second pulse signal, and the program may be set to independently vary the magnitudes and widths of the first and second pulse signals.

In the above electrode structure, two pulse signals may be the same or different. However, in order to prevent the signal applied from the electrode pad Pl1 from being returned through the electrode pad Pl2 or in order to prevent the signal applied from the electrode pad Pr1 from being returned to the electrode pad Pr2, it is preferable to multiplex the pulse signals to have a phase difference of 180°.

When a direct current is utilized as a current applied to the electrode pads Pl1, Pl2, Pr1, and Pr2, it is an advantage for strengthening the pelvic floor muscles to stimulate the nerve roots using an interrupted direct current. In a biphasic pulsating current, charged particles are periodically interrupted for a short time and flow bilaterally. It is well known that the above biphasic pulsating current is highly effective for electrical stimulation of nerves and electrical stimulation of nerve roots. Thus, when an alternating current is utilized, it is preferable to use the above biphasic pulsating current as the alternating current.

In general, the user sits on the device body B in a room. However, the user may hold the device body B on a toilet bowl in a bathroom and utilize the device of the present invention.

Thus, the device body B may be installed in various manners, and in the structure shown in FIG. 3, the user places the device body on a floor of a living room and sits naked on the device body.

However, if the user wishes to attach the device to a toilet bowl in a bathroom and utilize it, the user may place the device body B on a cover of the toilet bowl, which is already provided on the toilet body. Otherwise, as shown in FIG. 5, holes or protrusions may be provided at both sides of the device body and the device body may be coupled to a cover of the toilet bowl through the holes or the protrusions.

For example, the device body B can be rotatably coupled to the cover of the toilet bowl by means of a hinge to utilize the device body B if necessary. Rather than the cover of the toilet bowl, the device body B can be rotatably coupled to a bathroom article such as a bidet by means of a hinge to utilize the device body B. Here, when the device body B and the bidet are utilized together, it is preferable to dispose the operation panel part 5 consisting of the display unit and the circuit part for applying a control signal to the electrode pads P of the device body on an operation panel of the bidet.

In addition, it is preferable to provide a heating means, which can generate heat, on a seating part of an upper surface of the device body B.

The heating means may be constructed by embedding an electrical heater in the device body B or by embedding a resistance-heat type film in the device body to generate heat. In addition, by adding a low power laser function to the device body, it is possible to obtain a laser and low frequency heating function.

Meanwhile, FIG. 13 is a plan view of a device for strengthening the pelvic floor muscles according to another embodiment of the present invention.

Unlike the previous embodiment, the embodiment shown in this drawing is not provided with a contact preventing means, which is a through hole, formed at a portion of the device body B corresponding to the user's anus.

In this embodiment, one pair of the electrode pads are uniformly spaced from each other to form a first gap therebetween and a width of the first gap is approximately 10 mm to enhance a strengthening effect for the pelvic floor muscles. In addition, in order for the user not to feel a displeasure caused by electricity applied to his scrotum, a fan-shaped second gap corresponding to the user's scrotum is formed between the pair of the electrode pads and this second gap is widened at an angle of approximately 90°.

Remaining structures of this embodiment are the same as those of the previously illustrated embodiment, and description thereof is omitted.

Meanwhile, the previously illustrated embodiment has the structure in which a plurality of electrode pads are disposed on the same planar surface. However, the electrode pads may be disposed three-dimensionally to allow the electrode pads to be in contact with the user's muscle, and more accurately, the user's coccyx. Below, the embodiment in which the electrode pads are disposed three-dimensionally is illustrated.

Figure 14:
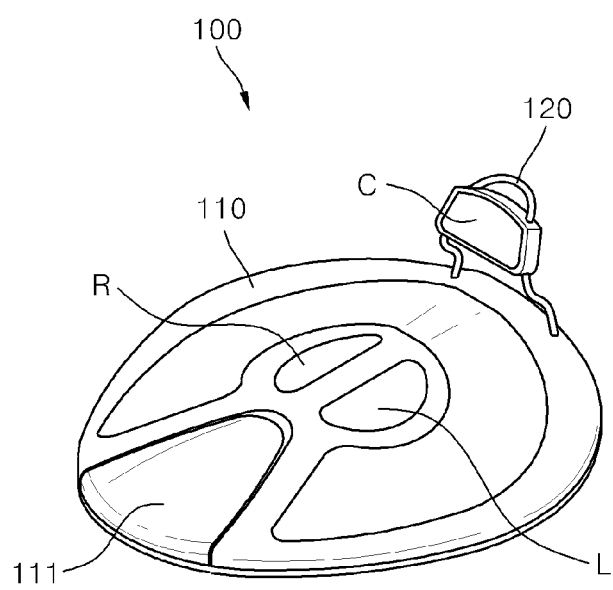
FIG. 14 is a schematic perspective view of a device for strengthening the pelvic floor muscles according to yet another embodiment of the present invention.
Figure 15:
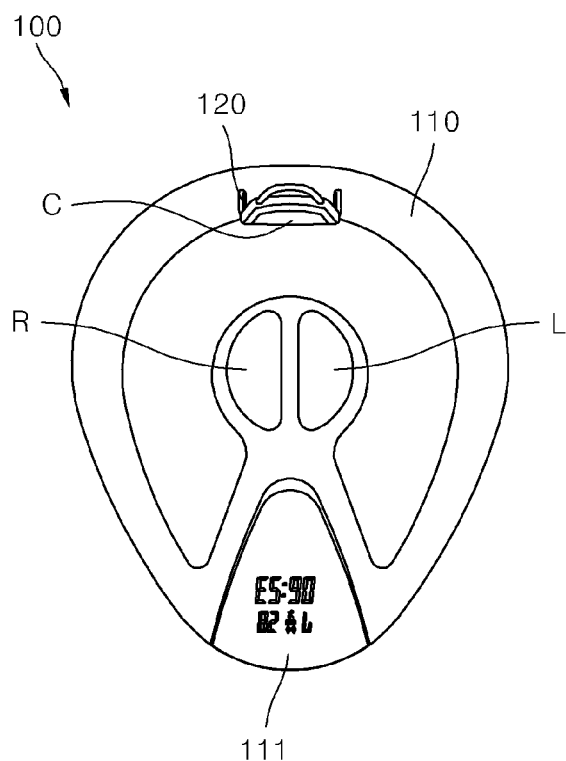
FIG. 15 is a schematic plan view of a device for strengthening the pelvic floor muscles shown in FIG. 14.
Figure 16:
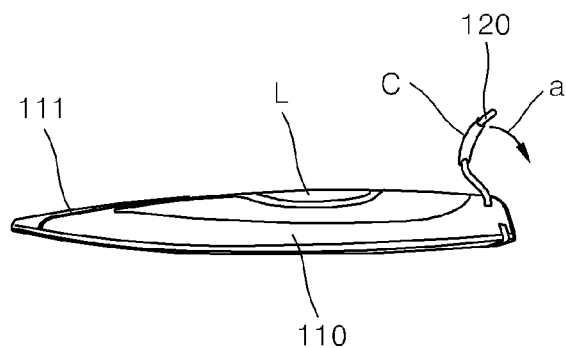
FIG. 16 is a schematic side view of a device for strengthening the pelvic floor muscles shown in FIG. 14.
Figure 17:
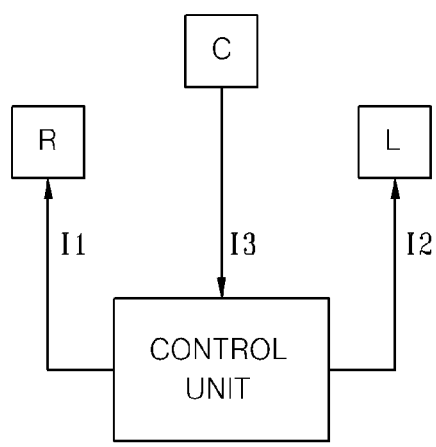
FIG. 17 is a circuit block diagram and a pulse signal waveform diagram.
Figure 17:
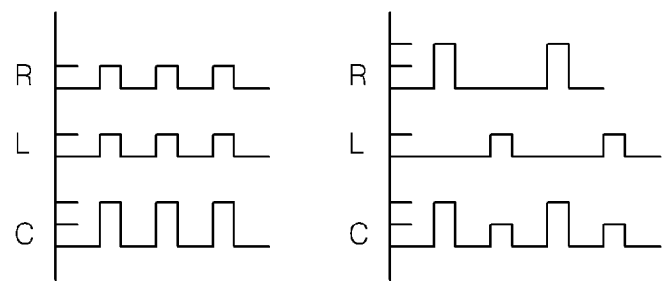

FIG. 14 is a schematic perspective view of a device for strengthening the pelvic floor muscles according to yet another embodiment of the present invention, FIG. 15 is a schematic plan view of a device for strengthening the pelvic floor muscles shown in FIG. 14, FIG. 16 is a schematic side view of a device for strengthening the pelvic floor muscles shown in FIG. 14 and FIG. 17 is a circuit block diagram and a pulse signal waveform diagram.

Referring to FIG. 14 to FIG. 17, a device 100 for strengthening the pelvic floor muscles according to this embodiment includes a main body 110, electrode pads R and L for the levator ani muscle, an electrode pad C for the coccyx, a contacting means and a control unit.

The main body 110 is a member on which the user sits and may be made of fibrous tissue or a synthetic resin. As shown in FIG. 15, a planar shape of the main body 110 may be an oval shape having a sharp front part in the direction that the user faces when sitting on the main body. As shown in FIG. 14, the main body 110 is formed such that a height gradually decreases from a center portion toward both side end portions.

If the main body 110 is inclined downward from the center portion toward both side end portions as described above, the user sitting on the main body can feel the stability and the levator ani muscles located at both sides of the anus can be effectively in contact with the main body.

On the other hand, an internal space is formed in a front end portion of the main body 110, and a control unit (for example, a printed circuit board) is disposed in this internal space. In addition, a display unit (for example, an LCD) for displaying a current time, an operating status and the like and an operating panel unit 111 having a switch for adjusting an intensity of the low frequency pulse and an operating time may be provided on the main body.

The electrode pads R and L for the levator ani muscle are provided to apply the electrical stimulation such as the low frequency pulse to the levator ani muscle. In the present embodiment, the pair of electrode pads R and L for the levator ani muscle are provided. Each of the electrode pads R and L for the levator ani muscle has a semi-circular shape, and the electrode pads R and L for the levator ani muscle are arranged on both sides of a central portion (that is, the highest line) of the main body 110 at a certain interval. The electrode pads R and L for the levator ani muscle are formed of a conductive material, and are hydrogel type electrodes, silicon+carbon coating type electrodes or metal electrodes. For example, a gel pad, carbon (carbon rubber) or a metal may be employed as a material for the electrode pad, and the electrode pad may be formed of a wet sponge.

The electrode pad C for the coccyx is provided for applying the electrical stimulation such as the low frequency pulse to the coccyx. Like the electrode pads for the levator ani muscle, the electrode pad C for the coccyx is formed of a conductive material, and is a hydrogel type electrode, silicon+carbon coating type electrode or metal electrode.

In the human body, the coccyx is located above the levator ani muscle. Thus, in order for the electrode for the coccyx to be in contact with the coccyx, the electrode pad for the coccyx is disposed above the electrode pads for the levator ani muscle. The detailed location of the electrode for the coccyx is illustrated in detail together with the contacting means.

The contacting means is provided to allow the electrode pad to be in contact with the coccyx of the human body. In this embodiment, the contacting means includes a supporting member 120. One end portion of the supporting member 120 is coupled to the main body 110 and the other end portion of the supporting member is disposed above the main body 110. In addition, since the electrode pad C for the coccyx is coupled to the other end portion of the supporting member 120, the electrode pad C for the coccyx is placed above the electrode pads R and L for the levator ani muscle. The supporting member 120 is constructed such that the supporting member has an "S" shape and can be bent rearward within a certain range indicated by the arrow (a) in FIG. 16. At this time, if the supporting member is formed of metal or plastic, the "S"-shaped supporting member 120 has an elastic force by which the bent supporting member is restored to its original state. Thus, if the user sits on the main body 110, the supporting member 120 is bent rearward according to a shape of a portion of the user's body corresponding to the coccyx. In this state, since the restitution force is exerted on the supporting member 120 to enable the supporting member to be restored forward (that is, to its original state), the electrode pad C for the coccyx comes in contact with the user's coccyx.

The control unit (not shown) is provided to apply the pulse signal to the electrode pad C for the coccyx and the electrode pads R and L for the levator ani muscle Like this embodiment, when the device has a total of three (3) electrode pads (two (2) electrode pads for the levator ani muscle and one (1) electrode pad for the coccyx), it is possible to transmit the pulse signal waveform shown in FIG. 17 to the electrode pads R and L for the levator ani muscle and the electrode pad C for the coccyx, so the low frequency is applied to the levator ani muscle and the coccyx of the user.

Meanwhile, a pulse method for applying the low frequency to the electrode pad may be varied according to the number and an arrangement of the electrode pads. In addition, a frequency band of the low frequency, a time for applying the low frequency and a cycle for applying the low frequency applying cycle may also be variously varied. However, the above characteristics are previously illustrated and the detailed description thereof is omitted.

In this embodiment, as described above, the electrode pad C for the coccyx is disposed above the electrode pads R and L for the levator ani muscle according to the body structure, that is, a relative location of the levator ani muscle and the coccyx, and when the user sits on the device, the electrode pad C for the coccyx is in close contact with the user's coccyx. Thus, compared to a conventional device, the low frequency pulse is more effectively applied to the user's coccyx. As a result, it is possible to effectively strengthen all of the pelvic floor muscles.

Figure 18:
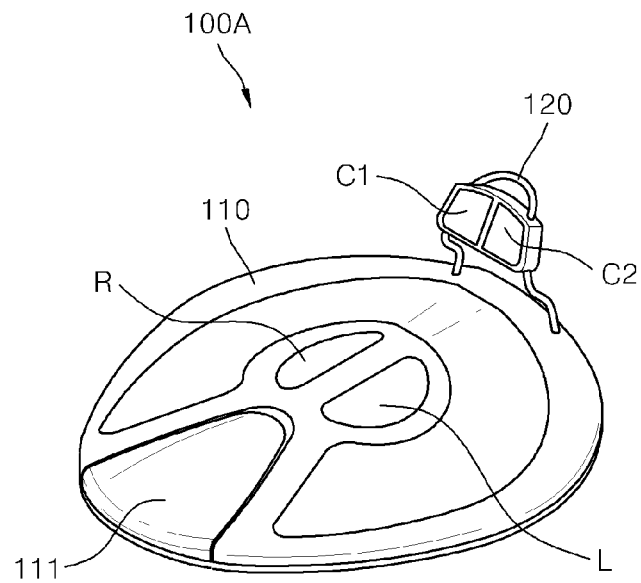
FIG. 18 is a schematic perspective view of a device for strengthening the pelvic floor muscles according to still another embodiment of the present invention.
Figure 19:
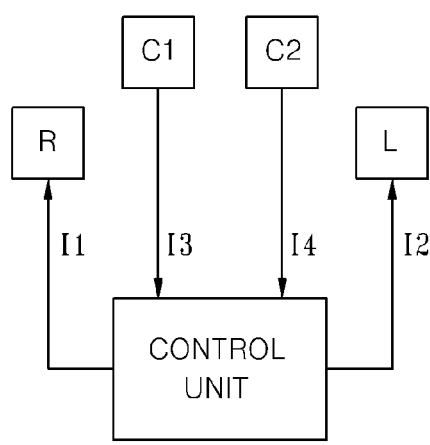
FIG. 19 is a circuit block diagram according to this embodiment.
Figure 20:
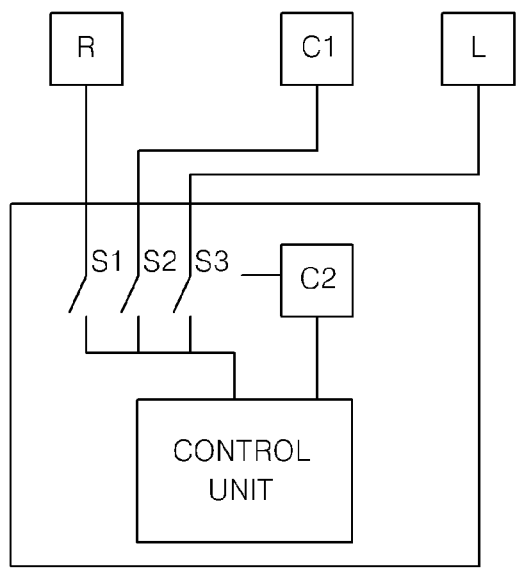
FIG. 20 is another circuit block diagram according to this embodiment.

FIG. 18 is a schematic perspective view of a device for strengthening the pelvic floor muscles according to still another embodiment of the present invention, FIG. 19 is a circuit block diagram according to this embodiment, and FIG. 20 is another circuit block diagram according to this embodiment.

Referring to FIG. 18 to FIG. 20, a device according to this embodiment is provided with a pair of electrode pads C1 and C2 for the coccyx. These electrode pads C1 and C2 for the coccyx are spaced apart and coupled to the supporting member 120.

When the electrode pad for the coccyx consists of a pair of electrode pads C1 and C2 for the coccyx, the circuit part may be constructed such that, as shown in FIG. 19, the electrode pad R for the levator ani muscle and the electrode pad C1 disposed at a right side form a pair and the electrode pad L for the levator ani muscle and the electrode pad C2 disposed at a left side form a pair for applying the low frequency pulse.

As shown in FIG. 20, by enabling the electrode pads to be switched, it is possible to apply the lower frequency three-dimensionally when the electrode pad is replaced with new one.

Figure 21:
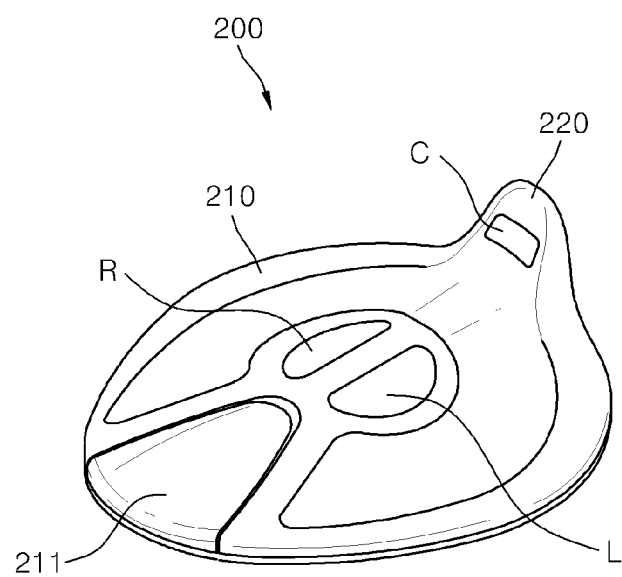
FIG. 21 is a schematic perspective view of a device for strengthening the pelvic floor muscles according to still another embodiment of the present invention.
Figure 22:
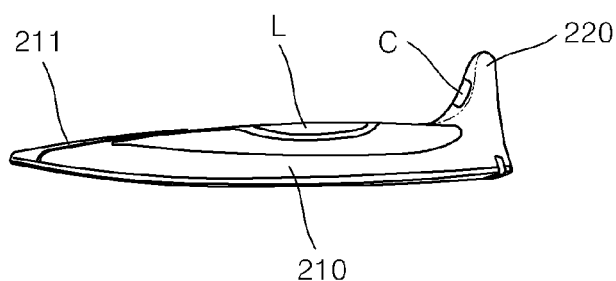
FIG. 22 is a schematic side view of a device for strengthening the pelvic floor muscles shown in FIG. 21.

FIG. 21 is a schematic perspective view of a device for strengthening the pelvic floor muscles according to still another embodiment of the present invention and FIG. 22 is a schematic side view of a device for strengthening the pelvic floor muscles shown in FIG. 21.

Referring to FIG. 21 and FIG. 22, a device 200 for strengthening the pelvic floor muscles according to this embodiment includes a main body 210, the electrode pads R and L for the levator ani muscle, the electrode pad C for the coccyx and the contacting means.

The main body 210 is a member on which the user sits and may be made of fibrous tissue or a synthetic resin. As shown in FIG. 21, a planar shape of the main body 210 may be an oval shape having a sharp front part in the direction in which the user faces when sitting on the main body. As shown in FIG. 21, the main body 210 is formed such that a height gradually decreases from a center portion toward both side end portions. If the main body 210 is inclined downward from the center portion toward both side end portions as described above, the user sitting on the main body can feel the stability and the levator ani muscles located at both sides of the anus can be effectively in contact with the main body.

On the other hand, an internal space is formed in a front end portion of the main body, and a control unit (for example, a printed circuit board) is disposed in this internal space. In addition, a display unit (for example, an LCD) for displaying a current time, an operating status and the like and an operating panel unit 211 having a switch for adjusting an intensity of the low frequency pulse and an operating time may be provided on the main body.

The electrode pads R and L for the levator ani muscle are provided to apply the electrical stimulation such as the low frequency pulse to the levator ani muscle. In the present embodiment, the pair of electrode pads R and L for the levator ani muscle are provided. Each of the electrode pads R and L for the levator ani muscle has a semi-circular shape, and the electrode pads R and L for the levator ani muscle are arranged on both sides of a central portion (that is, the highest line) of the main body 110 at a certain interval. The electrode pads R and L for the levator ani muscle are formed of a conductive material, and are hydrogel type electrodes, silicon+carbon coating type electrodes or metal electrodes. For example, a gel pad, carbon (carbon rubber) or a metal may be employed as a material for the electrode pad, and the electrode pad may be formed of a wet sponge.

The electrode pad C for the coccyx is provided to apply the electrical stimulation such as the low frequency pulse to the coccyx. Like the electrode pads for the levator ani muscle, the electrode pad C for the coccyx is formed of a conductive material, and is a hydrogel type electrode, silicon+carbon coating type electrode or metal electrode.

The contacting means is provided for contacting the electrode pad C for the coccyx to the coccyx in the body. In this embodiment, the contacting means includes a protrusion 220 formed of a material generating a restitution force, such as foam (rubber, polyurethane and the like). The protrusion 220 is coupled to a rear portion of the main body 210 and protrudes upward. The electrode pad C for the coccyx is coupled to this protrusion 220 so that the electrode pad C for the coccyx is disposed above the electrode pads R and L for the levator ani muscle.

In the device 200 for strengthening the pelvic floor muscle, if the user sits on the main body 110, the protrusion 220 is transformed according to a body shape of a site corresponding the user's coccyx as indicated by the phantom line in FIG. 22. Accordingly, the electrode pad C for the coccyx comes in contact with the user's coccyx. Thus, compared to a conventional device, the low frequency pulse is more effectively applied to a site corresponding to the user's coccyx. As a result, it is possible to effectively strengthen all of the pelvic floor muscles.

The device for strengthening the pelvic floor muscles and the method for controlling the above device according to the present invention are advantageous in that the pelvic floor muscles are strengthened by the electrical stimulation of the low frequency pulse so that the pelvic floor muscles of both men and women can b e stimulated electrically while contraction and a relaxation and rest time are repeated to strengthen the pelvic floor muscles of the body.

According to a strengthening of the pelvic floor muscles, various physical problems which are clinically revealed are solved, and smooth defecation, improvement of sexual function, prevention and treatment of urinary incontinence and massage of the prostate are promoted.

In addition, the device for strengthening the pelvic floor muscles of the present invention is advantageous in that even when the user does not have specialized knowledge about the pelvic floor muscles, the user can easily utilize the device at home to maximize a therapeutic effect and a strengthening effect.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A device configured to strengthen pelvic floor muscles, comprising;
a device body comprising;
a seat formed of an inflexible material and configured to allow a user to sit upon the seat;
two or more electrode pads configured to apply a low frequency electrical pulse, the two or more electrode pads configured to be disposed within the device body and configured to align with the users right and left ischia of a hip bone and a right and left sides of a perineum of the user during operation; and
a circuit part provided within the device body.

2. The device for strengthening a pelvic floor muscle of claim 1, further comprising a contact preventing through hole provided in a space between two or more electrode pads to prevent the device body from being in direct contact with the user's anus.

3. The device for strengthening a pelvic floor muscle of claim 1, wherein the seat includes a seating recess part which is depressed to allow the user to sit thereon.

4. The device for strengthening a pelvic floor muscle of claim 1, further comprising a remote controller performing a control process including a selection of a level of a strengthening training program, an intensity of the lower frequency pulse to be applied, and an operating time.

5. The device for strengthening a pelvic floor muscle of claim 4, wherein the remote controller is detachably coupled to the device body.

6. The device for strengthening a pelvic floor muscle of claim 1, wherein the circuit part is configured to apply a control signal to the electrode pads, the circuit part comprising a central processing unit performing a main controlling process, a key input unit which is an input part of a remote controller through which the user inputs data such as a band of a pulse, an applying time and a level set for a strengthening training program to a central processing unit, a display unit including an LED display for displaying input values and a current set status, a control program in which a status of the low frequency pulse is stored, the control program being programmed in the central processing unit of the device, an electrical signal generating unit for generating the low frequency pulse, and the electrode pad, provided on a printed circuit board (PCB).

7. The device for strengthening a pelvic floor muscle of claim 1, wherein the seat is formed of fibrous tissue or synthetic resin.

8. The device for strengthening a pelvic floor muscle of claim 1, wherein the electrode pad is formed of a silicon material and carbon coating material.

9. The device for strengthening a pelvic floor muscle of claim 1, wherein the device body is rotatably provided on a cover of a toilet bowl.

10. The device for strengthening a pelvic floor muscle of claim 1, further comprising a heating means, which can generate heat, provided on a seating part of an upper surface of the device body.

11. The device for strengthening a pelvic floor muscle of claim 1, wherein the electrode pads consists of two electrode pads, three electrode pads or four electrode pads so that the electrode pads receive and transmit the low frequency pulse passing through the resistance of the user's body between the right ischium and the left ischium to allow the pelvic floor muscle of the user's body to be stimulated.

12. The device for strengthening a pelvic floor muscle of claim 11, wherein the device includes first, second and third electrode pads and wherein the low frequency pulse is applied to the first and second electrode pads or the second and third electrode pads and wherein the third electrode pad is a central electrode and acts as a common return point.

13. The device for strengthening a pelvic floor muscle of claim 11, wherein the device includes first, second, third and fourth electrode pads and wherein a first pulse signal is applied to the first and third electrode pads and prevented from being returned to the second electrode pad and wherein a second pulse signal is applied to the second and fourth electrode pads prevented from being returned to the fourth electrode pad and wherein the first and second pulse signals have a phase difference of 180 degrees.

14. The device for strengthening a pelvic floor muscle of claim 13, wherein, if a direct current is applied to the four electrode pads, an interrupted direct current is utilized as the direct current and wherein, if an alternating current is applied to the four electrode pads, a biphasic pulsating current is utilized as the alternating current.

\* \* \* \* \*